United States Patent [19]

Ramsey, Jr. et al.

[11] Patent Number: 4,457,175
[45] Date of Patent: Jul. 3, 1984

[54] INSONIFICATION APPARATUS FOR AN ULTRASOUND TRANSMISSION SYSTEM

[75] Inventors: S. David Ramsey, Jr.; Jon C. Faenzer, both of Palo Alto, Calif.

[73] Assignee: Siemens AG, Berlin and Munich, Fed. Rep. of Germany

[21] Appl. No.: 378,858

[22] Filed: May 17, 1982

[51] Int. Cl.³ ............................................. G01N 29/04
[52] U.S. Cl. ........................................ 73/606; 128/660
[58] Field of Search ................. 73/606, 625, 642, 618; 128/660

[56] References Cited

U.S. PATENT DOCUMENTS

| | | | |
|---|---|---|---|
| 3,013,170 | 12/1961 | Sheldon | 73/618 |
| 3,431,462 | 3/1969 | Muenow et al. | 73/606 |
| 3,699,805 | 10/1972 | Bayre | 73/606 |
| 3,937,066 | 2/1976 | Green et al. | |
| 3,982,233 | 9/1976 | Green | |
| 4,386,612 | 6/1983 | Röder et al. | 73/642 |
| 4,387,599 | 6/1983 | Samodovitz | 73/642 |

OTHER PUBLICATIONS

J. F. Havlice, P. S. Green, J. C. Taenzer, W. F. Muller, "Spatially and Temporally Varying Insonification for the Elimination of Spurious Detail in Acoustic Transmission Imaging", *Acoustical Holography*, vol. 7, Plenum Publishing Corp., 1977, pp. 291–305.

*Primary Examiner*—Anthony V. Ciarlante
*Attorney, Agent, or Firm*—Karl F. Milde, Jr.

[57] ABSTRACT

The insonification apparatus is designed for the examination of an object, preferably for medical examinations. The apparatus contains an ultrasonic wave-generating transducer for emitting ultrasonic waves toward an examination plane, and an imaging device having principal planes for passing ultrasound waves received from the examination plane toward an imaging plane. The acoustic image formed in the imaging plane is received by a receiving transducer and transferred into electrical signals. The apparatus also contains an ultrasound condensing device such as a lens, a mirror, or a combination of such elements. This condensing device forms an ultrasonic image of the wave-generating transducer in the aperture of the imaging device. Thus, an increased uniformity of the intensity distribution in the image plane and an increased image contrast for high-spatial frequency information are obtained.

13 Claims, 8 Drawing Figures

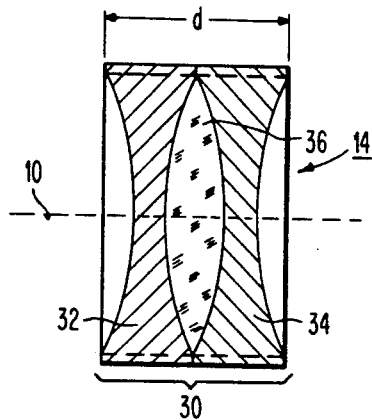
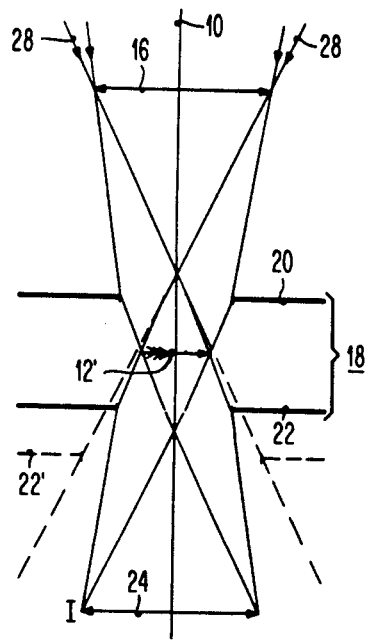
FIG. 3
FIG. 2
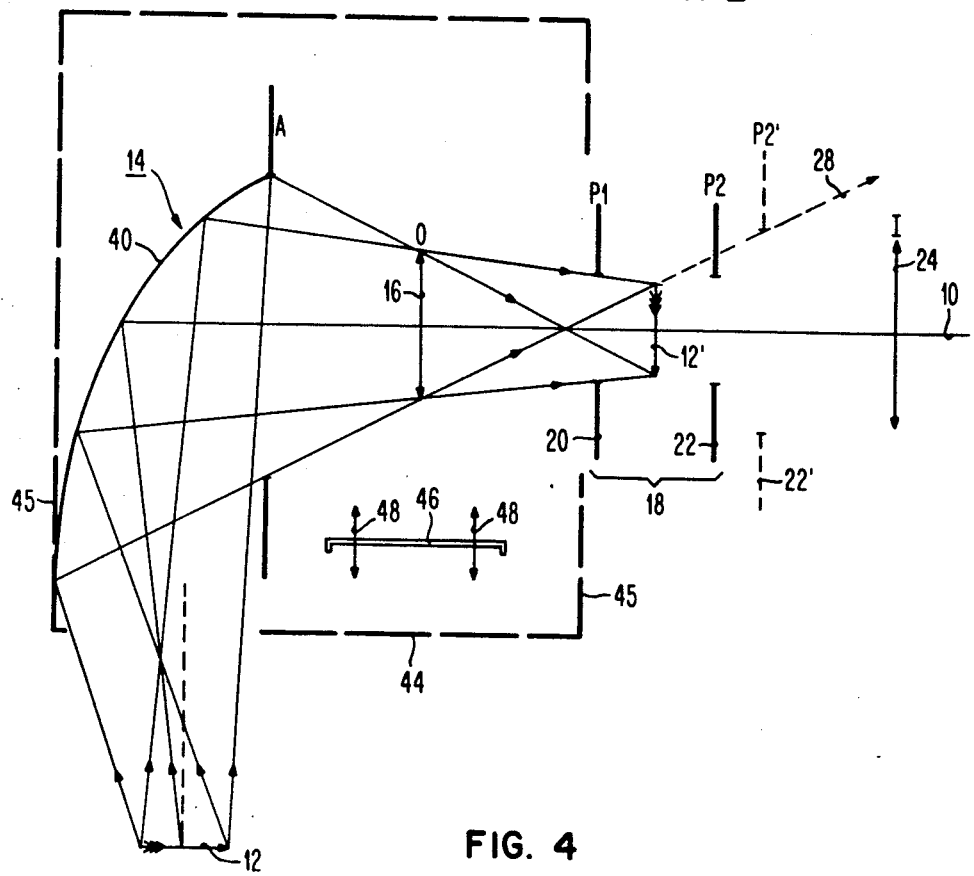
FIG. 4

INSONIFICATION APPARATUS FOR AN ULTRASOUND TRANSMISSION SYSTEM

BACKGROUND OF THE INVENTION

1. Field of the Invention

This invention relates to an ultrasound transmission imaging system or ultrasonic transmission camera. In particular this invention relates to the insonification apparatus or ultrasound transmitter of an ultrasound transmission system or camera. Still more particularly, this invention relates to the insonification apparatus of a C-scan ultrasound transmission system having an extended ultrasonic wave source. The insonification apparatus is preferably used for medical examinations of a patient.

2. Description of the Prior Art

An ultrasound transmission system incorporating an insonification apparatus of the type contemplated herein is described, for instance, in U.S. Pat. No. 3,937,066 and in the article by J. F. Havlice, P. S. Green, J. C. Taenzer and W. F. Mullen entitled "Spatially and Temporally Varying Insonification for the Elimination of Spurious Detail in Acoustic Transmission Imaging", published in *Acoustical Holography*, Vol. 7, Plenum Publishing Corrporation (1977), pp. 291–305.

In these prior art publications, real-time acoustic transmission imaging systems are described. Part of the attractiveness of transmission imaging lies in its orthographic image presentation. The images are readily interpretable. Since the images are formed by the attenuation properties of the tissues of a patient under examination, the images may contain diagnostically significant information.

In the aforementioned article in *Acoustical Holography*, supra, imaging with diffuse sound is suggested. An extended ultrasonic wave-generating transducer, in particular a multi-element transmitting array, is used to reduce spurious detail in the acoustic images produced by the imaging lens.

However, it has been found that the contrast or spatial resolution of the acoustic images of such an ultrasound transmission system can be improved even more. A measure of spatial resolution is the so-called "modulation transfer function", as is well-known in the imaging art. Therefore, there is the strong desire to improve the modulation transfer function of the system.

Due to the fact that in diffuse insonification sound waves impinge into the object plane from a large number of directions, shadowing effects due to out-of-plane objects are largely eliminated. In the prior art article in *Holography*, supra, it is expressly stated that each point of the object plane is insonified "from many directions". Yet, in order to improve the performance of the system, the object plane should receive ultrasound waves preferably from all directions. In other words, each point in the image should contain information from each and every transmitter element of the ultrasound wave-generating transducer. In fact, it has been found that in the prior art insonification system full advantage has not been taken of the wide angular acceptance angles of the imaging lens.

In addition, it has been found that the image field is not insonified uniformly (when no object is present). Thus, another problem of the prior art design resides in the fact that the image produced from the object plane shows a sharp decline of the intensity towards its edges. In other words, there is a predominance of intensity in the center of the image (in the absence of the object). Yet, it is desirable to have an image in which the intensity is equally distributed across the image.

Composite acoustic lens assemblies which are adapted for use in a fluid medium and utilized for forming acoustic images with incident acoustic waves coming from an object under examination are disclosed in U.S. Pat. No. 3,982,223.

SUMMARY OF THE INVENTION

1. Objects

It is an object of this invention to provide an insonification apparatus for an ultrasound transmission system having an improved overall performance.

It is another object of this invention to provide an insonification apparatus for an ultrasound transmission system having an increased image contrast for high-spatial frequency information.

It is still another object of this invention to provide an ultrasonic orthographic transmission camera having an increased uniformity of the insonification of an object under examination.

It is still another object of this invention to provide a C-scan transmission and insonification system in which the distribution of the intensity is substantially uniform across the image produced by the imaging device.

2. Summary

According to this invention, an insonification apparatus for an ultrasound transmission system contains an ultrasonic wave-generating transducer or source for emitting ultrasonic waves. The transducer is preferably an extended ultrasound source equipped for diffuse insonification. In the ultrasound transmission system is provided an examination plane which contains a plane of an object under examination. This examination plane receives ultrasonic waves from the ultrasonic wave-generating transducer. The ultrasound transmission system also contains an imaging device such as an imaging lens or an imaging lens system, which imaging device has an aperture of a predetermined width for passing ultrasound waves therethrough. This imaging device receives ultrasonic waves from the examination plane.

The insonification apparatus contains an ultrasound collecting or condensing device which is positioned between the ultrasonic wave-generating transducer and the examination plane. This condensing device is designed for directing ultrasonic waves from the ultrasonic wave-generating transducer through the examination plane towards the imaging device. The condensing device thereby forms an ultrasonic image of the ultrasonic wave-generating transducer. The transducer image should be located (at least approximately) within the aperture of the imaging device.

By employing a condensing device positioned between the ultrasonic source and the object, a larger amount of ultrasonic waves passes through the entrance aperture of the imaging device and thereby contributes to the image of the object under examination. Each point in the image can now contain information from every transducer element of the ultrasound wave generating transducer. Thus, insonification of the object plane is provided such that the ultrasonic rays fill the available angular coverage and improve the field uniformity in the image plane. By using basically all of the available angular coverage, the response of the imaging system to high spatial frequency components is increased, i.e., the modulation transfer function of the system is improved, as compared to the prior art.

As a condensing device, there may be used any known reflecting or refracting element, such as a mirror or a lens, respectively. There may also be used a combination of reflecting and refracting elements to achieve the desired goal.

The ultrasonic condensing device preferably may comprise a first and a second ultrasonic condensing lens and a filling located between these two lenses. The first and second condensing lenses may have a high ultrasonic velocity as compared to the filling.

The foregoing and other objects, features and advantages of the invention will be apparent from the following more particular description of preferred embodiments of the invention, as illustrated in the accompanying drawings.

BRIEF DESCRIPTION OF THE DRAWINGS

In the drawings:

FIG. 2 is a portion of FIG. 1 showing various rays in more detail;

FIG. 3 is an ultrasonic condensing device comprising two condensing lenses and a filling inbetween, which device may be used in an ultrasound transmission system;

FIG. 4 is an embodiment of an insonification system in which the condensing device is a single off-axis mirror;

DETAILED DESCRIPTION OF THE PREFERRED EMBODIMENTS

Figure 1:
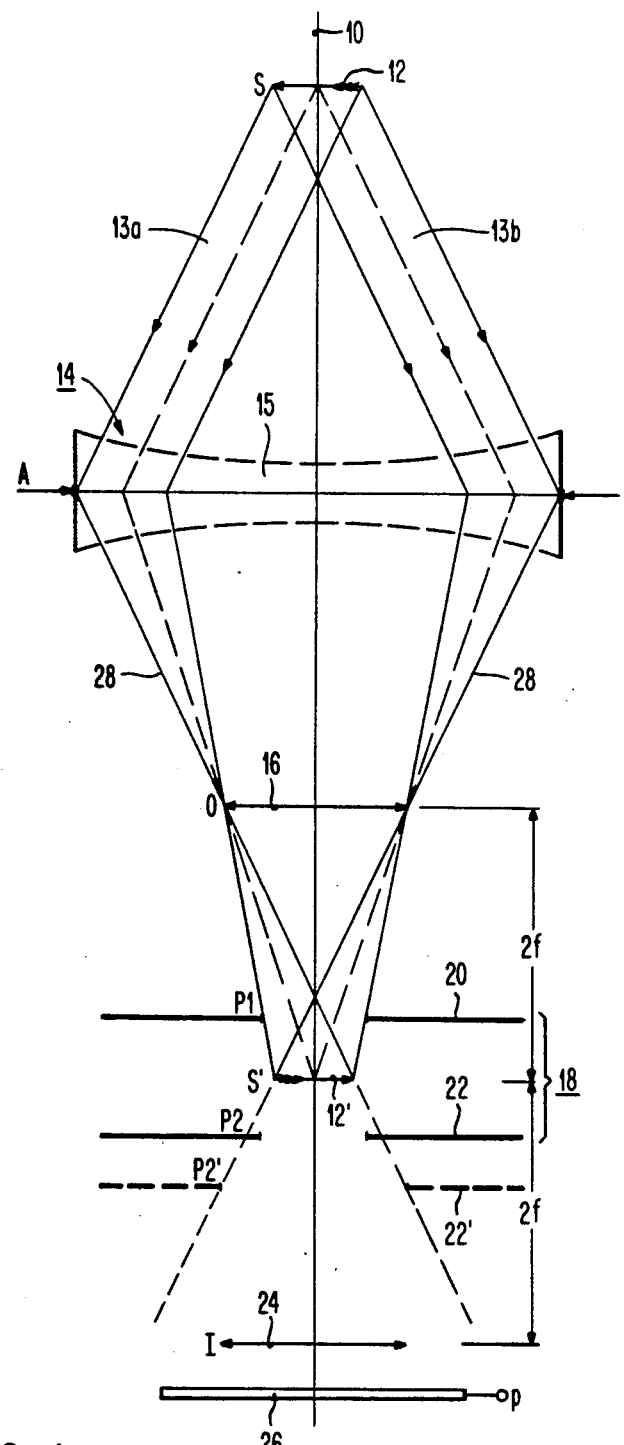
FIG. 1 is a schematic diagram of a transmission insonification system incorporating a C-scan camera transmitter or C-scan transmission insonification apparatus and a condensing device.

In FIGS. 1 and 2, a C-scan ultrasound transmission system containing an insonification apparatus is schematically illustrated. The insonification apparatus incorporates a collecting or condensing device, as will be explained subsequently in more detail. Studies have shown that a condensing device for the C-scan camera transmitter is effective in improving the field uniformity in the image plane and also in increasing the image contrast of high spatial frequency information in the object.

FIG. 1 shows only the basic concepts of such a condensing device incorporated into the insonification apparatus of an ultrasound transmission system which is primarily used for medical purposes. The acoustic axis of the system is denoted by 10. In the embodiment according to FIGS. 1 and 2, the acoustic axis 10 is straight.

An ultrasonic wave-generating source or transducer 12 is provided for emitting ultrasonic waves. The transducer 12 which is indicated by an arrow has the diameter S. Preferably the transducer 12 is a large or extended incoherent source which is equipped for diffuse insonification. The transducer 12 may comprise a large number of small continuous incoherent transmitter elements, as is well-known in the art.

In FIGS. 1 and 2, insonification is from top to bottom. The ultrasonic waves emitted by the transducer 12 are collected by a condensing device generally denoted by 14. In FIG. 1, two bundles of ultrasonic rays 13$a$ and 13$b$ are illustrated. The rays in each bundle 13$a$, 13$b$ happen to be parallel to each other. It will be understood, however, that the insonification is diffuse, and that the transducer 12 emits ultrasonic waves in all directions.

In particular, the device 14 may be a condensing lens 15. The ultrasound condensing device 14 is positioned between the ultrasonic wave-generating transducer 12 and an examination plane 16. In the examination plane 16 there is positioned an object under examination. That is, in medical examinations there is placed the plane of interest of the patient. The examination plane 16 receives ultrasonic waves from the ultrasonic wave-generating transducer 12 via the ultrasound condensing device 14. As can be seen, all points in the examination plane 16 are illuminated by each point in the transducer 12.

The condensing device 14 has an aperture A, and the usable size of the examination plane is denoted by O. Thus, the size O denotes the maximum object size that can be examined.

There is also provided an imaging device 18 which receives ultrasonic waves from the examination plane 16. This imaging device 18 contains at least one aperture of predetermined width for passing ultrasound therethrough. In the present embodiment, it is assumed that the imaging device 18 is a well-known lens system comprising two lenses each being represented by its principal lens plane 20 and 22, respectively. The apertures of these lenses are P1 and P2, respectively. The transmission system may also include a well-known scanning device (not shown). Preferably, such scanning device may be included in the imaging lens system 18, but such scanning device is not an essential element of this invention. The scanning device may be arranged between the lenses 20 and 22 and may comprise two counter-rotating prisms. Such a package of lenses and prisms is disclosed in U.S. Pat. No. 3,913,061 which patent is incorporated herein by reference.

The waves from the transducer 12 are collected by the condensing device 14 and brought to focus inside the imaging lenses 20 and 22. In other words, an ultrasonic image 12' is formed of the ultrasonic wave-generating transducer 12. This image 12' is located in the aperture of the imaging device 18. The image 12' has a diameter designated by S'. In the illustrated embodiment, the image 12' is located approximately midway between the two lenses 20 and 22.

The arrangement is such that the projected image 12' of the transducer 12 appears within the aperature of the imaging device 18. In other words, the entire aperture of the imaging device 18 is filled with the image of the transducer 12.

The imaging device 18 generates an image 24 of the object 16. The image size is denoted by I. In the image plane, there is positioned an ultrasound receiving transducer 26 of well-known design. This receiving transducer 26 preferably may be curved. For the sake of clarity, this transducer 26 is shown removed from the plane of the image 24. The receiving transducer 26 converts the acoustic image field received from the imaging device 18 into electrical signals p.

In FIGS. 1 and 2 the imaging system 18 is positioned a distance $2f$ away from the examination plane 16, wherein f is the focal length of the imaging system 18. The image 24 of the object plane is similarly spaced away a distance $2f$ from the imaging system 18. This will result in unit magnification O:I=1:1 between the object 16 and its image 24. This unit magnification may be employed in order to keep the complexity of the ultrasound system low. However, also other magnifications O:I may be chosen.

The diameter A of the condensing device 14 is determined by the marginal rays 28 that are passed through the edges of the object plane 16 and the imaging device 18 (lenses 20, 22). For the transmission system illustrated in FIGS. 1 and 2, the limiting aperture of the imaging system 18 is actually the image 22' of the aperture P2 of the second lens 22 as imaged by the first lens 20. This virtual image 22' having the larger aperture P2' is shown in dotted lines. The image 22', therefore, characterizes the size and the location of the aperature P2 as seen through the lenses 20 and 22.

An important feature of the condensing device 14 is that every point in the object plane 16 is insonified by every element of the transmitting array 12. Also, because the image 12' of the transmitting transducer 12 just fills the aperture of the receiving lens system 18, any ray passing through a point in the object plane 16 from the transmitter array 12 is assured of contributing to the image 24 of the object 16. In addition, an increased angular insonification is provided by the condensing device 14. This insures that the image contrast at all spatial frequencies is limited basically only by the imaging system 18 containing the lenses 20 and 22. The uniformity of the object insonification is improved since every point in the object plane 16 is insonified by every element of the source 12. Moreover, the rays from the wave-generating transducer 12 are directed by the condensing device 14 such that a very efficient use is made of the available transducer energy, i.e., little energy passing through the object plane 16 is not gathered by the lens system 18 and used to form the image 24.

As in well-known systems, the object 16 may be positioned in an ultrasound guiding fluid (not shown) the velocity of sound of which matches the sound velocity in the object. For instance, a patient to be examined may be immersed into a water tank.

As far as the physical parameters of the system are concerned, also another consideration has to be taken into account. The object plane 16 should be spaced some distance away from the condensing device 14 in order to allow for object placement and maneuvering space.

In FIG. 1, a single refracting element or lens 15 is shown as the condensing device 14. This ultrasound condensing lens 15 is built like an optical dispersing lens. It may be a Fresnel lens. It is, however, understood that also lens assemblies or systems assembled from several lenses may be used as the condensing device 14. This will be explained in more detail with reference to FIG. 3. The ultrasound condensing device 14 may also be an ultrasound condensing mirror or a combination of a lens and a mirror or of lenses and mirrors.

Various lens and/or mirror materials may be applied. Due to its high acoustic velocity, aluminum is a lens material which may be used if a high index of refraction is desired. Aluminum lens elements can be fabricated easily. Other useful lens materials include polystyrene and beryllium. A mirror material which may be used is a closed-cell plastic foam.

It has already been mentioned that instead of a single refracting element 15 (shown in FIG. 1), a system of refracting elements may be applied. An example of such a condensing lens system is illustrated in FIG. 3 and will be explained later.

Generally speaking, for the purposes of the present invention, a condensing lens assembly or system may be employed which is composed of two or more lens elements. An embodiment of a condensing lens assembly 30 is illustrated in FIG. 3.

The illustrated assembly 30 is an on-axis lens system which is symmetrical to the acoustic axis 10. It includes two condensing lenses 32 and 34 with a filling 36 in the space therebetween. The lenses 32 and 34 may be identical. The space between the lenses 32 and 34 which is taken by the filling 36 is shaped like an optical magnification glass. Due to its shape and its index of refraction, the filling 36 constitutes a bi-convex lens, that is, a converging lens. Likewise, due to their shapes and high index of refraction, the lenses 32 and 34 constitute bi-concave lenses that are also converging elements. Thus, the indices of ultrasound refraction are selected such that the overall system 32 through 36 constitutes a condensing lens system.

The three-lens system 30 according to FIG. 3 may preferably include two condensing lenses 32 and 34 made of aluminum and a filling 36 which is a fluorocarbon liquid, in particular fluorinated hydrocarbon. A liquid which has been found useful as filling 36 in conjunction with aluminum lenses 32 and 34 is sold under the name FC-75 by the 3M Co., U.S.A.

In the three-lens system 30 illustrated in FIG. 3, the ultrasound waves will first enter a condensing medium of high velocity of ultrasound, then a condensing medium of low velocity of ultrasound, and finally again a condensing medium of high velocity of ultrasound. Due to the large difference of the indices of refraction at the boundaries between the three materials, at each boundary a large ultrasound deflection takes place, and therefore the lens system 30 can be kept comparatively small. In other words, the thickness d may be kept relatively small, while the lens system 30 still has a refraction strength sufficient for the condensing purposes of the present invention.

For test purposes a condensing device 14 in accordance with FIG. 3 has been designed. The condensing device 14 has a focal length of 64.1 cm, a diameter of 55.3 cm, and a total edge thickness of 15 cm. Quarter-wave matching layers to reduce reflections are attached to the surfaces. These matching layers (not shown) have acoustic impedance values of $Z=5$ at the water-/aluminum surface and of $Z=4.3$ at the aluminum/hydrocarbon surface. The incidence angles at the refracting surfaces are kept as small as possible to suppress mode conversion to shear waves. Losses have been compensated to some extent by increasing the transducer power. It must be taken into consideration that losses will increase as a function of the lens radius due to the changing refraction angles.

In FIGS. 1 and 2 an on-axis ultrasound system has been shown, but this is only one of several possibilities. In FIG. 4 an ultrasound transmission system is illustrated which uses as its condensing device 14 an off-axis acoustic mirror 40, in particular a spherical mirror. This condensing device 14 eliminates most mode-conversion and critical angle problems encountered with refracting components. It also eliminates the thick cross sections of the individual lens elements at their edges and removes the possibility of multiple reverberations between lens surfaces. The trade-offs that must be made are that the reflector 40 must be comparatively large and that there may be some small shading across the object plane 16.

According to FIG. 4, the reflector or mirror 40 is insonified in a diffused manner by the extended ultrasonic wave-generating transducer 12. Insonification is from the lower portion of FIG. 4 to the upper portion, and reflection is to the right side of FIG. 4. FIG. 4 may either represent a plan view or a side view of the ultrasound transmission system. That is, two different designs are possible. The patient under examination is again positioned in the object plane 16. The ultrasound condensing device 14 directs ultrasonic waves from the transducer 12 through the examination plane 16 toward the imaging device 18. Again the condensing device 14 forms an ultrasonic image 12' of the transducer 12. This transducer image 12' is located approximately half-way between the apertures P1, P2 of the imaging device 18. The image of the object 16 is again denoted by 24.

The mirror 40 is provided with an exit aperture 42. This aperture 42 is symmetrical with respect to the main or acoustic axis 10. The diameter of the aperture 42 is A. It will be noted that the emitting transducer 12 is located below and to the left of the plane of the aperture 42.

The space between the condensing device 14 and the imaging device 18 may be filled by a fluid such as water. Walls which define the examination space and which, in one of the two different designs, may be provided for holding the fluid are designated by the numerals 44, 45. The patient is immersed into the fluid in the space between the aperture 42 and the imaging device 18. If FIG. 4 represents a side view according to one of the two different designs, there may be provided a platform 46 for the patient to sit or stand in the tank formed by the walls 44, 45. This platform 46 may be movable up and down, as indicated by double arrows 48. The mirror 40 may constitute a portion of the tank walls 45.

It has been mentioned that the mirror 40 may be a spherical off-axis mirror. However, the mirror 40 may also be of a parabolic or ellipsoidal or of any other concave shape which ensures that the ultrasound waves are focused between the apertures P1, P2 of the imaging device 18. If an ellipsoidal shape is chosen, one focal point of the ellipsoid may be located in the middle portion of the transducer 12, and the other focal point may be located in the middle portion of the transducer image 12'.

One of the advantages of the condensing device 14 of FIG. 4 over that of FIGS. 1 through 3 resides in the compactness of the entire ultrasound transmission system.

For test purposes, a condensing device 14 in accordance with FIG. 4 has been designed. This condensing device 14 was determined to work in conjunction with an ultrasound transmission system which is described in U.S. Pat. No. 4,433,690 issued Feb. 28, 1984 (Green). The reflector 40 has a spherical surface with a diameter of 102 cm and a radius of curvature of 105 cm. The input and output acoustic axis of the reflector form an angle of 78.2°. The reflector 40 itself may be fabricated from sheet aluminum with a thin layer of closed-cell foam to form the reflecting surface.

The design constraints of such a reflecting condensing device 14 are that no rays enter the space bounded by the plane of the aperture 42 prior to being reflected by acoustic mirror 40, as shown in FIG. 4. This is to prevent transmitted rays from being intercepted by a subject or the movable floor before being reflected by the condensing mirror 40.

Another advantage of the condensing device 14 illustrated in FIG. 4 is that no quarter-wave matching layers are required. Also, multiple reflections cannot occur in the reflector device 14 as presented.

The illumination field leaving the condensing lens 15 (see FIG. 1) or the reflector 40 (see FIG. 4) can also be generated by an ultrasonic array transducer located where the lens or refractor would be. Appropriate electronic delay drive circuitry would cause the acoustic output from the array to be an excellent simulation of the condensing system output. Though more complex mechanically and electronically, such a system would be even more compact.

Figure 5:
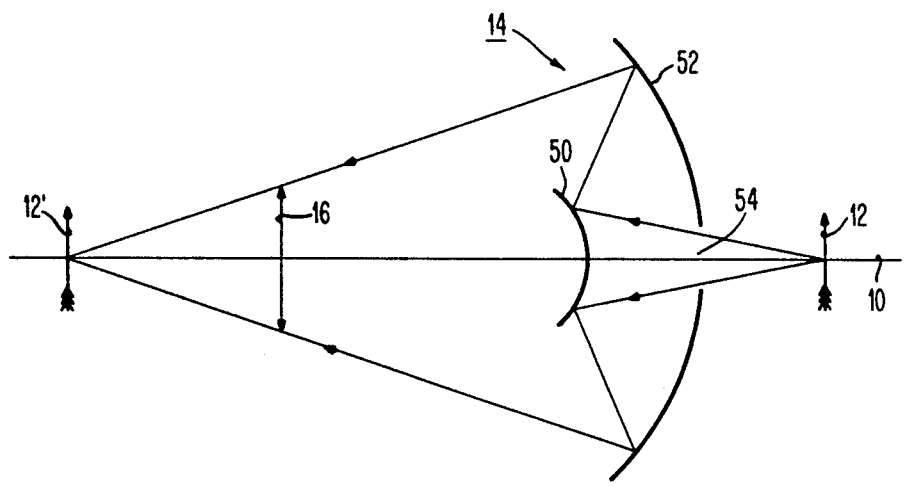
FIG. 5 is an embodiment of an insonification system in which the condensing device is formed by two mirrors which are arranged symmetrically with respect to an imaging axis.

In FIG. 5 another embodiment of an ultrasound transmission system containing an insonification condensor apparatus is schematically illustrated. In this embodiment the insonification apparatus is an on-axis dual mirror system. In particular, the condensing device 14 contains a smaller convex mirror 50 and a larger concave mirror 52 which are both symmetrical with respect to the main acoustic axis 10 which is straight. In this embodiment insonification from the transducer 12 is from right to left. The larger concave mirror 52 contains an aperture 54 through which ultrasound waves from the transducer 12 are directed to the convex surface of the smaller mirror 50. Here the waves are reflected towards the concave surface of the larger mirror 52. Subsequently, the ultrasound waves are reflected from the concave mirror 52 through the object plane 16 to form an image 12' on the axis 10.

The arrangement of the two mirrors 50 and 52 in FIG. 5 is similar to a Cassagranian system which is commonly used in telescopes. As in the optical field, the larger mirror 52 may be a parabolic mirror, whereas the smaller mirror 50 may be a hyperbolic mirror. It will be realized that in such a symmetrical system the image 12' is upright.

Figure 6:
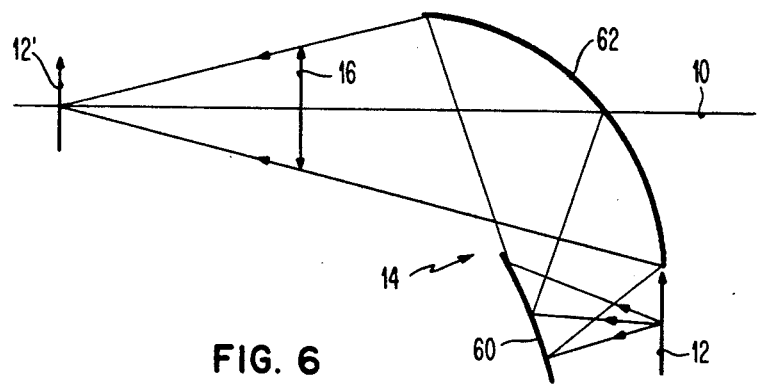
FIG. 6 is an embodiment of an insonification system in which the condensing device is formed by two mirrors in an off-axis arrangement.

An ultrasound transmission system containing another embodiment of a condensing device 14 is illustrated in FIG. 6. It can be termed as an off-axis dual mirror system. In this embodiment there are provided a convex mirror 60 and a concave mirror 62. The transducer 12 emits ultrasound waves which are reflected from the convex mirror 60 towards the concave mirror 62. The concave mirror 62 focuses the ultrasound waves in an image 12' of the source after transmission through the object plane 16. Insonification is again from right to left.

Figure 7:
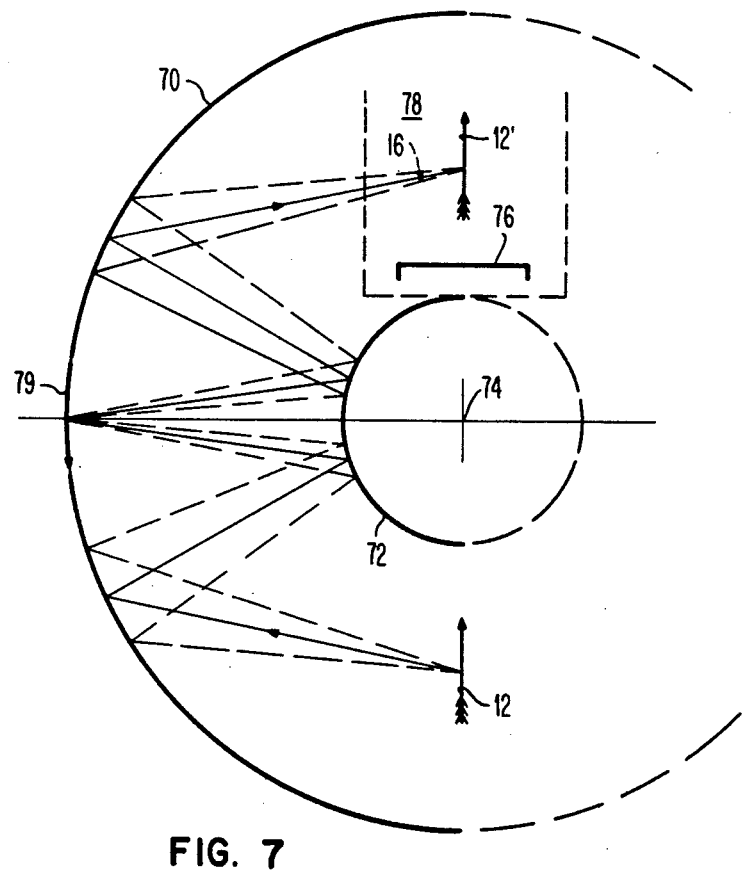
FIG. 7 is an embodiment of an insonification system in which two mirrors are arranged concentrically to each other and off an imaging axis.

In FIG. 7 still another embodiment of an insonification apparatus containing a condensing system 14 is illustrated. This condensing device 14 is an off-axis two mirror system with intermediate image. This condensing device 14 has good focusing properties and provides for a sharp image of the transducer 12.

In particular, the device 14 contains a larger spherically concave mirror 70 and a smaller spherically convex mirror 72. Both mirrors 70, 72 are arranged concentrically with respect to a center 74. In the cross section of FIG. 7, both mirrors 70 and 72 are shown as portions of circles around the center 74. The transducer 12 as well as the transducer image 12' are located on a line passing through the center 74. FIG. 7 may represent a plan view or a side view of the ultrasound transmission system. If FIG. 7 represents a side view, there may be provided a stand 76 for a patient. This stand 76 may be positioned in a tank which constitutes the patient room 78. In this version, the transducer 12 is positioned under the patient.

The embodiment according to FIG. 7 has the property that an intermediate image 79 of the transducer 12 is generated on the inner wall of the larger mirror 70. This image 79 is slightly distorted. Nevertheless, imaging of this intermediate image 79 between the mirror 72 and the mirror 70 creates a source image 12' of good quality.

Figure 8:
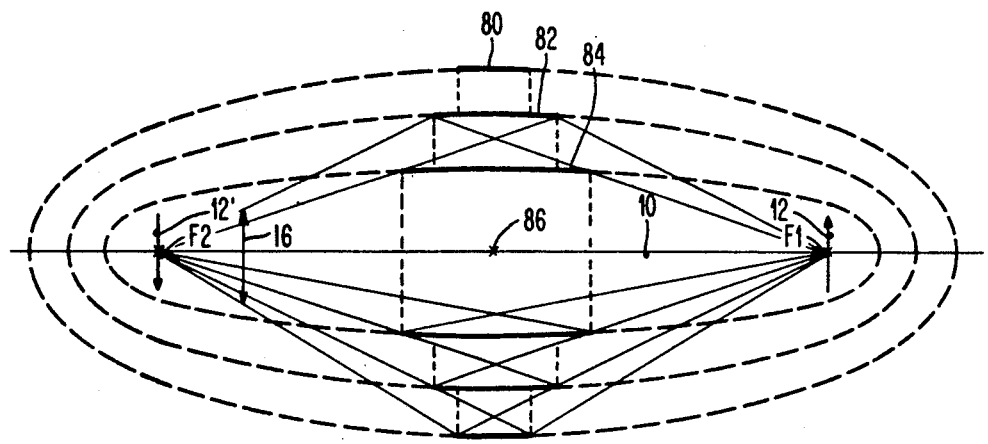
FIG. 8 is an embodiment of an insonification system in which the condensing device comprises a plurality of symmetrically arranged relecting rings which represent parts of ellipsoids.

In FIG. 8 an embodiment of an insonification system is illustrated which is also an on-axis system. The acoustical axis is again denoted by 10. This embodiment contains a number of mirrors which are rings of ellipsoids. In FIG. 8 three such rings 80, 82 and 84 are illustrated. The three ellipsoids are stretched out in the direction of the acoustical axis 10. These rings 80 through 84 are arranged symmetrically with respect to the acoustical axis 10. They have different diameters. It will be noted that the outer ring 80 is smaller than the middle ring 82, and that the middle ring 82 again is smaller than the inner ring 84. The center of the rings 80, 82 and 84 is denoted by 86. All three rings 80 through 84 have the same first focus F1 and the same second focus F2. The arrangement is such that the transducer 12 is positioned in the first focus F1. As a result, the image of the transducer 12' is positioned in the second focus F2. The embodiment shown in FIG. 8 has the advantage that there are no reverberations and that the design may be compact and symmetrical.

One of the advantages of the incorporation of a condensing device or system is the achievement of a larger intensity uniformity in the image of the object. Another advantage is that the time delay between various ultrasound waves which arrive at the object plane has become smaller. That is, the difference in time between wave fronts which are emitted from the ultrasound source at the same time is considerably reduced on their arrival at the object plane. Thus, it is possible to produce an image in a shorter period of time. Also, a better rejection of objects which are not positioned in the focal plane may be observed. That is, there is achieved an increased blurr for out-of-focus objects. Another advantage resides in the fact that the modulation transfer function of the ultrasound imaging system is improved. In other words, the image contrast for high-spatial frequency information has been increased as compared to a system without a condensing device.

While the forms of the insonification apparatus and transmission system herein described constitute preferred embodiments of the invention, it is to be understood that the invention is not limited to these precise forms of assembly, and that a variety of changes may be made therein without departing from the scope of the invention.

What is claimed is:

1. An insonification apparatus for an ultrasound transmission system, said system being determined for the examination of an object, comprising in combination:
    (a) an ultrasonic wave-generating transducer for emitting ultrasonic waves;
    (b) an examination plane containing a plane of said object under examination, said examination plane receiving ultrasonic waves from said ultrasonic wave-generating transducer;
    (c) an imaging device having an aperture of predetermined width for passing ultrasound therethrough, said imaging device receiving ultrasonic waves from said examination plane; and
    (d) an ultrasound condensing device positioned between said ultrasonic wave-generating transducer and said examination plane for directing ultrasonic waves from said ultrasonic wave-generating transducer through said examination plane toward said imaging device, thereby forming an ultrasonic image of said ultrasonic wave-generating transducer which transducer image is located in said aperture of said imaging device, such that it completely fills the entire aperture of the imaging device.

2. The insonification apparatus according to claim 1, wherein said ultrasound condensing device comprises at least one ultrasonic condensing lens.

3. The insonification apparatus according to claim 1, wherein said ultrasonic condensing device comprises an assembly of ultrasonic lenses.

4. The insonification apparatus according to claim 3, wherein said ultrasonic condensing device comprises a first and second ultrasonic condensing lens and a sound-conducting filling between said first and second lenses.

5. The insonification apparatus according to claim 4, wherein said first and second condensing lenses have a high ultrasonic velocity as compared to said filling.

6. The insonification apparatus according to claim 5, wherein said condensing lenses contain aluminum, and wherein said filling contains a fluorinated hydrocarbon.

7. The insonification apparatus according to claim 3, wherein said lenses are arranged along a straight optical axis.

8. The insonification apparatus according to claim 1, wherein said ultrasonic condensing device comprises at least one ultrasonic reflector.

9. The insonification apparatus according to claim 8, wherein said ultrasonic reflector is a condensing mirror.

10. The insonification apparatus according to claim 1, wherein said ultrasonic wave-generating transducer comprises a plurality of independent ultrasound sources.

11. An insonification apparatus for an ultrasound transmission system, said system being determined for the examination of an object, comprising in combination:
    (a) an ultrasonic wave-generating transducer for emitting ultrasonic waves;
    (b) an examination plane containing a plane of said object under examination, said examination plane receiving ultrasonic waves from said ultrasonic wave-generating transducer;
    (c) an imaging device having an aperture of predetermined width for passing ultrasound therethrough, said imaging device receiving ultrasonic waves from said examination plane; and
    (d) an ultrasound condensing device positioned between said ultrasonic wave-generating transducer and said examination plane for directing ultrasonic waves from said ultrasonic wave-generating transducer through said examination plane toward said imaging device, thereby forming an ultrasonic image of said ultrasonic wave-generating transducer which transducer image is located in said aperture of said imaging device, such that it completely fills the entire aperture of the imaging device;

wherein said imaging device is an imaging lens system containing two converging lenses, and wherein said ultrasonic image of said ultrasonic wave-generating transducer is formed between said two converging lenses.

12. An ultrasound transmission system for examination of an object, comprising in combination:
   (a) an insonification apparatus containing
      (a1) an ultrasonic wave-generating transducer for emitting ultrasonic waves;
      (a2) an examination plane for placing a plane of said object under examination therein, said examination plane receiving ultrasonic waves from said ultrasonic wave-generating transducer;
      (a3) an imaging device having an aperture of predetermined width for passing ultrasound therethrough, said imaging device receiving ultrasonic waves from said examination plane;
      (a4) an ultrasound condensing device positioned between said ultrasonic wave-generating transducer and said examination plane for directing ultrasonic waves from said ultrasonic wave-generating transducer through said examination plane toward said imaging device, thereby forming an ultrasonic image of said ultrasonic wave-generating transducer which transducer image is located in said aperture of said imaging device, such that it completely fills the entire aperture of the image deivce; and
   (b) an ultrasonic receiving transducer for converting at least a portion of an acoustic image field received from said imaging device into electrical signals, said receiving transducer being positioned such that said imaging device forms an image of said examination plane on said ultrasonic receiver transducer.

13. An insonification apparatus for an ultrasound transmission system, said system being determined for the examination of an object, comprising in combination:
   (a) an ultrasonic wave-generating transducer for emitting ultrasonic waves;
   (b) an examination plane containing a plane of said object under examination, said examination plane receiving ultrasonic waves from said ultrasonic wave-generating transducer;
   (c) an imaging device having an aperture of predetermined width for passing ultrasound therethrough, said imaging device receiving ultrasonic waves from said examination plane; and
   (d) an ultrasound condensing device positioned between said ultrasonic wave-generating transducer and said examination plane for directing ultrasonic waves from said ultrasonic wave-generating transducer through said examination plane toward said imaging device, thereby forming an ultrasonic image of said ultrasonic wave-generating transducer which transducer image is located in said aperture of said imaging device, such that it completely fills the entire aperture of the imaging device;

wherein said imaging device is positioned a distance 2f away from the examination plane, wherein f is the focal length of the imaging device.

* * * * *

UNITED STATES PATENT AND TRADEMARK OFFICE
CERTIFICATE OF CORRECTION

PATENT NO. : 4,457,175

DATED : July 3, 1984

INVENTOR(S) : S. David Ramsey, Jr. et al

It is certified that error appears in the above-identified patent and that said Letters Patent is hereby corrected as shown below:

On the title Item /75/ should read:

-- /75/ Inventors: S. David Ramsey, Jr.; Jon C. Taenzer, both of Palo Alto, Calif. --

Signed and Sealed this

Fifth Day of March 1985

[SEAL]

Attest:

DONALD J. QUIGG

Attesting Officer  Acting Commissioner of Patents and Trademarks